US006498862B1

(12) United States Patent
Pierson et al.

(10) Patent No.: US 6,498,862 B1
(45) Date of Patent: Dec. 24, 2002

(54) EVALUATION OF BIOFILMS AND THE EFFECTS OF BIOCIDES THEREON

(75) Inventors: Duane L. Pierson, Houston, TX (US); David W. Koenig, Menasha, WI (US); Saroj K. Mishra, Houston, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/316,913

(22) Filed: May 18, 1999

(51) Int. Cl.[7] ................................................ G06K 9/00
(52) U.S. Cl. .................................... 382/133; 435/288.7
(58) Field of Search ................................ 382/133, 128, 382/173; 702/21; 348/79; 356/335; 250/573; 435/30, 32, 287.1, 288.1, 288.7

(56) References Cited

U.S. PATENT DOCUMENTS

| | | | | |
|---|---|---|---|---|
| 5,003,611 A | | 3/1991 | Miyake et al. | 382/6 |
| 5,049,492 A | | 9/1991 | Sauer et al. | 435/30 |
| 5,051,359 A | * | 9/1991 | Characklis | 435/32 |
| 5,112,745 A | | 5/1992 | Lorr | 435/38 |
| 5,290,701 A | | 3/1994 | Wilkins | 435/312 |
| 5,349,874 A | | 9/1994 | Schapira et al. | 73/864 |
| 5,356,521 A | | 10/1994 | Nekoksa et al. | 204/153.12 |
| 5,372,936 A | * | 12/1994 | Fraatz et al. | 435/34 |
| 5,444,527 A | | 8/1995 | Kosaka | 356/73 |
| 6,130,956 A | * | 10/2000 | Butterworth et al. | 382/100 |
| 6,195,443 B1 | * | 2/2001 | Hammond et al. | 382/100 |
| 6,317,511 B1 | * | 11/2001 | Horiuchi | 382/133 |

OTHER PUBLICATIONS

David W.Koenig, S. K. Mishra, & Duane L. Pierson, "Removal of Burkholderia Cepacia Biofilms with Oxidants." *Biofouling*, Apr. 3, 1995, vol. 9, pp. 51, 52, 54–61.

Ted Selinsky, *Tech Brief Magazine*, "Apparatus Measures Attachment or Detachment of Biofilm," Oct. 10, 1995.

* cited by examiner

*Primary Examiner*—Andrew W. Johns
(74) *Attorney, Agent, or Firm*—James M. Cate

(57) ABSTRACT

Biofilm formation is monitored by real-time continuous measurement. Images are formed of sessile cells on a surface and planktonic cells adjacent the surface. The attachment of cells to the surface is measured and quantitated, and sessile and planktonic cells are distinguished using image processing techniques. Single cells as well as colonies are monitored on or adjacent a variety of substrates. Flowing streams may be monitored. The effects of biocides on biofilms commonly isolated from recyclable water systems are measured.

34 Claims, 18 Drawing Sheets

Untouched Image
(Phase Contrast Microscope, $3000\ \mu m^2$ Field of View)

Binary Image
(Background subtraction and binary conversion)

*Burkholderia cepacia*
Adhesion Sequence

START

1 HOUR

2 HOURS

3 HOURS

4 HOURS

5 HOURS

First Image (Start of Sequence)

Luminance Threshold: 127-255

Cell Number: 149

Coverage: 232 $\mu m^2$

Second Image Taken 10 Seconds After First (Fig. 8A)

Luminance Threshold: 127-255

Cell Number: 133

Coverage: 250 $\mu m^2$

Stored Image (Average of FIGS. 8A and 8B)

Luminance Threshold: 127-255

Cell Number: 98

Coverage: 190 $\mu m^2$

| PLOT | PHASE OF EXPERIMENT |
|---|---|
| A | Adhesion |
| B | Treatment with 12 ppm of Chlorine |
| C | Adhesion |
| D | Treatment with 24 ppm of Chlorine |
| E | Adhesion |
| F | Treatment with 48 ppm of Chlorine |

EVALUATION OF BIOFILMS AND THE EFFECTS OF BIOCIDES THEREON

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

This invention relates to biofilm measurement and the efficacy of biocides on microbes.

Water processing systems including regenerative water processing systems are susceptible to formation of biofilm. Unless countermeasures are taken, microbes may colonize the interior surfaces and aqueous flow lines of these systems. Microbial biofilms can cause both process and health-related problems. Control or elimination of them is required to prevent adverse effects. Pathogenicity is of primary concern for human consumption, while additional concerns focus on the phytotoxic nature of bacterial contaminants.

Biofilm bacteria have been isolated from water lines and in potable water systems. These biofilms may harbor pathogens as well as microbial strains having resistance factors that could affect health. Therefore, delivery of potable hygienic water of acceptable quality is requisite for reliance upon water processing systems. Microbial contamination and biofilm development in water storage and distribution systems thus must be controlled possibly long periods of time.

Remediation methods are continually being sought to disinfect and remove biofilms from water lines. One proposed biocide (disinfection agent) for water systems is iodine. However, iodine may allow the development of resistant strains. For example, a four year test of a ground-based model of a spacecraft potable-water system showed that iodine treatment can limit planktonic microbes, but biofilms developed despite biocide treatment. Other tests have shown that increased resistance to disinfection results from attachment to or association of microbes with various surfaces of the water system.

Paramount to the treatment of biological depositions is the ability to monitor the microbial attachment process. Sessile organisms usually are monitored by either direct enumeration of viable bacteria, indirect enumeration using fluid frictional resistance measurements, colorimetric viability measurements, or electrical measurements. Other monitoring methods have also been employed.

Effective alternative remediation methods may, however, require a true understanding of colonization events and physiological factors that influence bacterial adhesion. This understanding may be aided by monitoring either adhesion or the effect of biocides on sessile bacteria continuously, without halting growth. Whether biofilm-control procedures are compatible with closed or open water processing environments is a primary consideration.

Unlike some water-treatment protocols, the use of toxic, potentially corrosive, or noxious chemicals may not be possible in closed environments. Other constraints may limit the types of chemicals and methods that can be used to treat water systems. These constraints may arise from limitations on space, power, and time. Further constraints may be imposed by other factors. For example, system design may dictate whether various chemicals can be used in the treatment system without adversely affecting the system itself.

Ideally, biocide/biofilm control agents should kill the target organism quickly and remove a wide variety of bacteria including spores and biological debris. In addition, the agents should not produce toxic residues or be harmful to the system itself. There may be no single chemical agent or procedure that meets these criteria at the present time. Several agents, each with specific biological-control capabilities, may, therefore, be required to do the job.

SUMMARY OF THE INVENTION

In general, in one aspect, the invention features an apparatus for monitoring particulate matter in a fluid container or conduit. The apparatus may include a wall portion that supports sessile particles derived from the fluid. The apparatus may also include means for forming images of the sessile particles and particles in the fluid adjacent the wall portion and means for digitizing and processing data corresponding to the images and for producing an output data segment corresponding to the sessile particles present in the images. The apparatus may further include means for processing the output data segment and deriving an output signal corresponding to the accumulation of sessile particles on the wall portion.

In general, in another aspect the invention features an apparatus for monitoring microbial matter within a fluid container. The apparatus may include a wall portion that supports sessile organisms derived from organisms present in the fluid. The apparatus may also include means for forming images of sessile organisms adhered to the wall portion and planktonic organisms in the fluid adjacent the wall portion and means for digitizing and processing data corresponding to the images and for producing an output data segment corresponding to the sessile organisms present in the images. The apparatus may further include means for processing the output data segment and deriving an output signal corresponding to the accumulation of sessile organisms on the wall portion.

In general, in another aspect, the invention features a method of monitoring particulate matter. The method may include supporting sessile particles derived from a fluid and forming images of the sessile particles and particles in the fluid adjacent the wall portion. The method may also include processing data corresponding to the images to produce an output data segment corresponding to the sessile particles present in the images and to derive an output signal corresponding to the accumulation of sessile particles.

In general, in another aspect, the invention features a method of monitoring microbial matter within a fluid container. The method may include supporting sessile organisms derived from organisms present in the fluid on a surface of the container and forming images of the sessile organisms adhered to the surface and planktonic organisms in the fluid adjacent the surface. The method may also include processing data corresponding to the images to produce an output data segment corresponding to the sessile organisms present in the images and to derive an output signal corresponding to the accumulation of sessile organisms on the surface of the container.

Implementations of the invention may also include one or more of the following: assessing the effect of an agent on sessile particles; and assessing the effect of biocide on sessile organisms.

Implementations of the invention may offer the advantage of processing liquids for the treatment of microbes without loss of water from a closed system.

Other features and advantages will become apparent from the following description, drawings, and from the claims.

DESCRIPTION

The invention relates to a "real time" continuous optical biofilm measurement system. Implementations of the invention may measure the attachment of cells (e.g. single cells) to a surface, may distinguish between planktonic and sessile cells, and may provide a quantitative measurement of the attached cells (surface growth) or biofilms. Implementations of the invention may provide a direct measurement of cells attached to a surface. Implementations of the invention may quantify individual cells as well as colonies, may be applicable to a variety of substrates, for example, glass, silicon, plastic, organic polymers (acrylimide, teflon, agar), metals (stainless, aluminum, titanium), carbon composites, etc., and may also be used for monitoring sessile bacteria in flowing streams. Implementations of the invention may be used to measure the effects of oxidizing biocides (disinfection agents) on biofilm bacteria commonly isolated from water systems.

Implementations of the invention may be used in monitoring and process control for biofilm and/or planktonic particle formation and removal. Potential applications include their use in, for example, cooling towers, paper processing, the semiconductor industry, medical hardware manufacturing, and the bottled water industry. Moreover, these implementations may be used for developmental marketing evaluations in the biocide industry.

Figure 1:
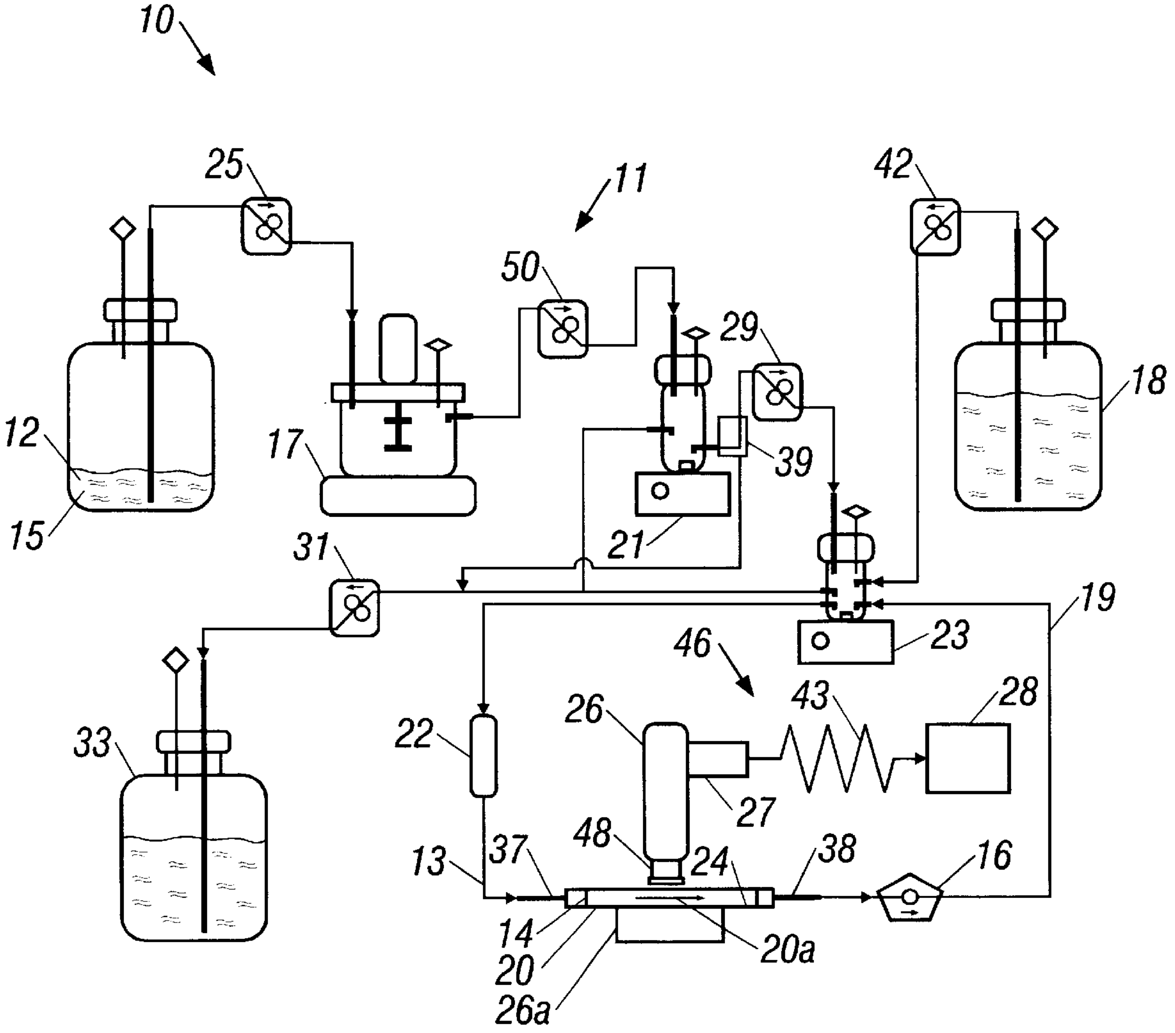
FIG. 1 is a representation of an apparatus for monitoring water-borne microbes that have attached themselves to a surface in accordance with an embodiment of the invention.

A system 10, in accordance with an embodiment of the invention, is shown in FIG. 1. System 10 may be used to measure biofilm formation and cell adhesion rates on a wetted surface 24 using automated image analysis for monitoring of the real-time cell-to-surface attachment rate. System 10 permits continual direct measurement and allows for a kinetic description of the attachment process. Modification of system 10 may allow direct quantification of biocide efficacy against biofilms, as will be discussed below.

System 10 includes a source 11 of water containing a suspension of microbes (particles) 12. The source 11 includes a growth medium 15 (e.g., a hydrated growth medium), a fermentor 17, an adapter valve 39 (e.g., a three-way adapter valve) which may be used if isolation of a recirculation loop 19 is required from source 11, a mixing vessel 21, and a mixing vessel 23. The growth medium 15 is used to grow microbes. A pump 25 is coupled between the growth medium 15 and fermentor 17 for pumping a suspension of the grown microbes from the growth medium 15 to the fermentor 17. The fermentor 17 is used to further grow microbes at much higher density. A pump 50 is coupled between the fermentor 17 and mixing vessel 21 to pump a higher density suspension of microbes from the fermentor 17 to the mixing vessel 21. The higher density suspension of microbes supplied to mixing vessel 21 is mixed with previously supplied microbes (suspension) in mixing vessel 21 through the action of pump 50 and a pump 29 coupled between mixing vessel 21 and mixing vessel 23. A source 18 of water (e.g., deionized water) is coupled to mixing vessel 23 through a pump 42 which may be used to adjust microbe concentration in mixing vessel 23. A pump 31 is coupled between mixing vessel 23 and a waste tank 33 which is used to discard excess microbe suspension from system 10. Pump 31 is also coupled to adapter valve 39 to discard excess microbe suspension from system 10 when adapter valve 39 is so activated. A growth-containing liquid 13 may be diluted or concentrated in mixing vessel 23 with water from source 18 and pumped with a pump 16 (e.g., a high speed pump) through a flow chamber and an optical cell (FOC) 20 of system 10. The flow stream may be dampened with a pulse dampener 22 (e.g., of 1-mL total volume) positioned upstream of the flow chamber 20. The pulse dampener 22 may be a 1.0 ml reaction vial that has two needles inserted through a septum. The vial holds approximately 0.5 ml of fluid (e.g., fluid 13) while in operation and allows for dampening of the pump 16 pulsing such that the fluid flows in a continuous rate through the chamber 20.

The system 10 may be operated in still or flowing water systems for water quality monitoring. For example, the system 10 may be installed such that the optical measurement chamber 20 is positioned in-line with any fluid process stream (examples include water treatment, cooling towers, paper machines, beverage processes, etc.) The system 10 may then be used to monitor the microbial quality of the stream by direct measurements.

The adhesion of biological depositions on inner wall portion (surface 24) of the chamber 20 may be measured quantitatively by an optical and image processing system 46. The surface 24 forms part of a glass/spacer sandwich 14 (spacer may be, for example, silicon) of the FOC 20. The system 46 includes a microscope 26, a camera 27 (e.g., an SIT camera), and image processing equipment 28 which receives video signal output from camera 27. Optical and image processing system 46 is shown in more detail in FIG. 2. Image processing equipment 28 includes a camera controller 47 coupled to camera 27 for controlling camera 27, an image processor 30 (e.g., an ARGUS 10 image processor available from Hamamatsu Corporation) coupled to camera controller 47, a frame grabber/image processor 32 coupled to image processor 30, a video monitor 34 coupled to the frame grabber/image processor 32, a storage device 35 (e.g., an optical storage disk or device) coupled to the frame grabber/image processor 32, and a plotting or display device 36 coupled to the frame grabber/image processor 32.

Figure 2:
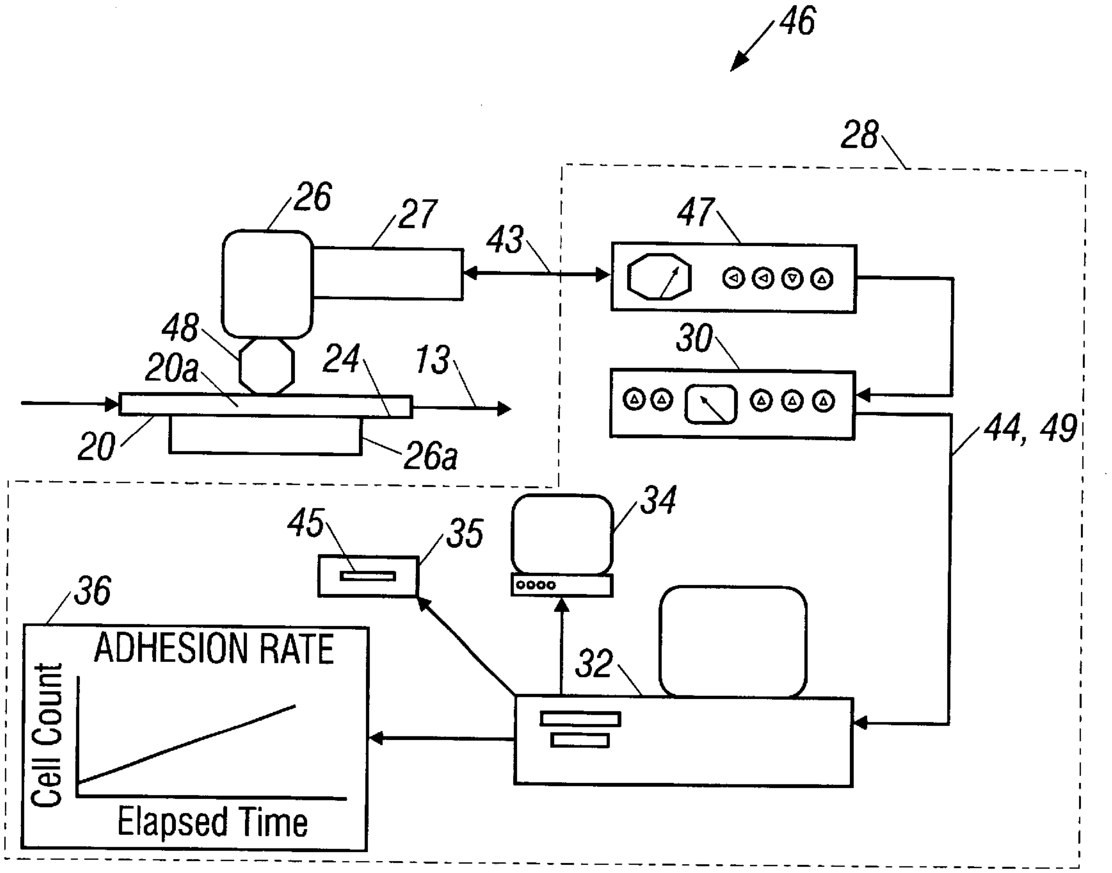
FIG. 2 is a representation of an apparatus for an optical and image processing system in accordance with an embodiment of the invention.
Figure 3:
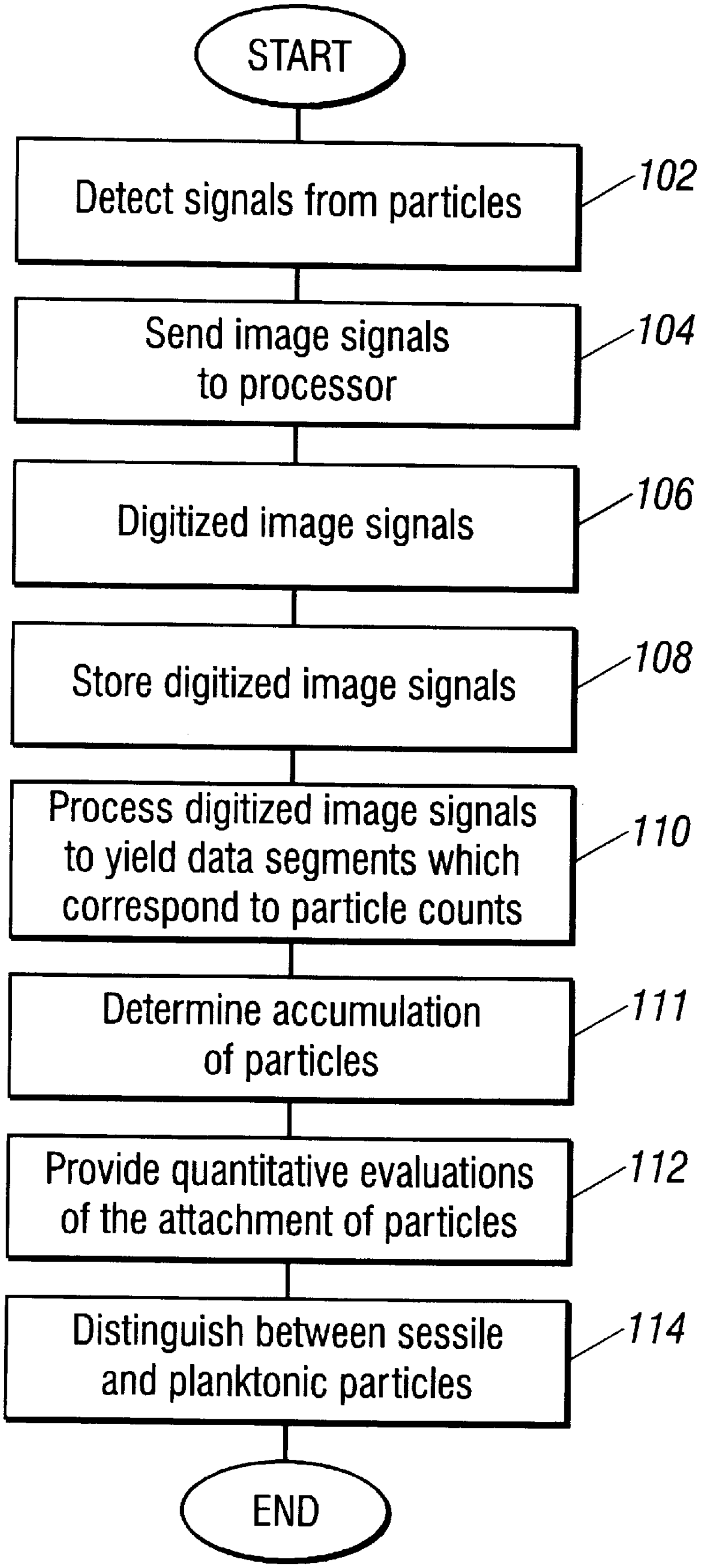
FIG. 3 is a flowchart of a method for monitoring particulate matter in accordance with an embodiment of the invention.

Referring to FIGS. 1–3, microscope 26 is focused on surface 24 of the FOC 20 which is supported on microscope stage 26*a* of microscope 26. Camera 27 is coupled to (mounted on) microscope 26 to convert images from the field of view of the microscope 26 focused on surface 24 to video signals. The camera 27 may detect 102 signals above a threshold intensity level from sessile particles attached to the surface 24 in the FOC 20 and from particles (planktonic particles) in the suspension (fluid 13) adjacent the surface 24 in the FOC 20. The camera 27 is controlled by the camera controller 47 and the output of the camera 27 corresponding to the detected signals is fed 104 through controller 47 and processor 30 to the frame grabber/image processor 32. The camera 27, controller 47, processor 30, and grabber/processor 32 may filter and remove data segments corresponding to intensity levels below the threshold level. The processor 30 may be, for example, a real time system that allows for background subtraction and image enhancement in real-time. The grabber/processor 32 allows, for example, for automated analysis of images such that objects (cells) can be enumerated and sized.

The resulting image data are digitized 106 in grabber/processor 32 and stored 108 in the storage device 35 and processed 110 by grabber/processor 32 to yield data segments which correspond to cell counts as a function of time. The grabber/processor 32 may do this by counting objects which were imaged in the field of view of the microscope 26. By using object size and shape factors, the grabber/processor 32 discriminates between cells and other objects in the field of view. From these data segments, an output signal is derived 111 which corresponds to the accumulation of sessile particles on surface 24. The output signal may be plotted on device 36.

The system 10 may provide 112 quantitative evaluations of the attachment of biofilm cells (microbes, particles, or particulate matter) 12 to surface 24 in real time, if desired, and may distinguish 114 planktonic and sessile cells, through the use of image processing techniques. For example, planktonic cells may be eliminated in measurements during normal biofilm analysis of sessile cells by averaging two or more images taken at different times and then subtracting the portion of the average due to the planktonic cells (e.g., subtracting group portions of the averaged image below a predetermined "white" intensity threshold which includes the planktonic cell information but not the sessile cell information). In alternative embodiments, planktonic cell analysis may be desirable to measure planktonic it may only require an inverse calculation used to measure attached cells. When images are averaged because the planktonic cells have moved in time their averaged images appear to be of lower intensity or "gray" and, therefore, are distinguishable from the averaged images of the sessile cells which appear white. In other words, in order to track or trend the planktonic cells, after averaging two or more images, as above, the white portion of the averaged image which includes the sessile cell information is subtracted (i.e., subtraction occurs) instead of the gray portion which includes the planktonic cell information. Biofilm formation and cell adhesion rates may, therefore, be measured directly with the use of optical microscopy and image analysis using the above techniques.

Figure 3A:
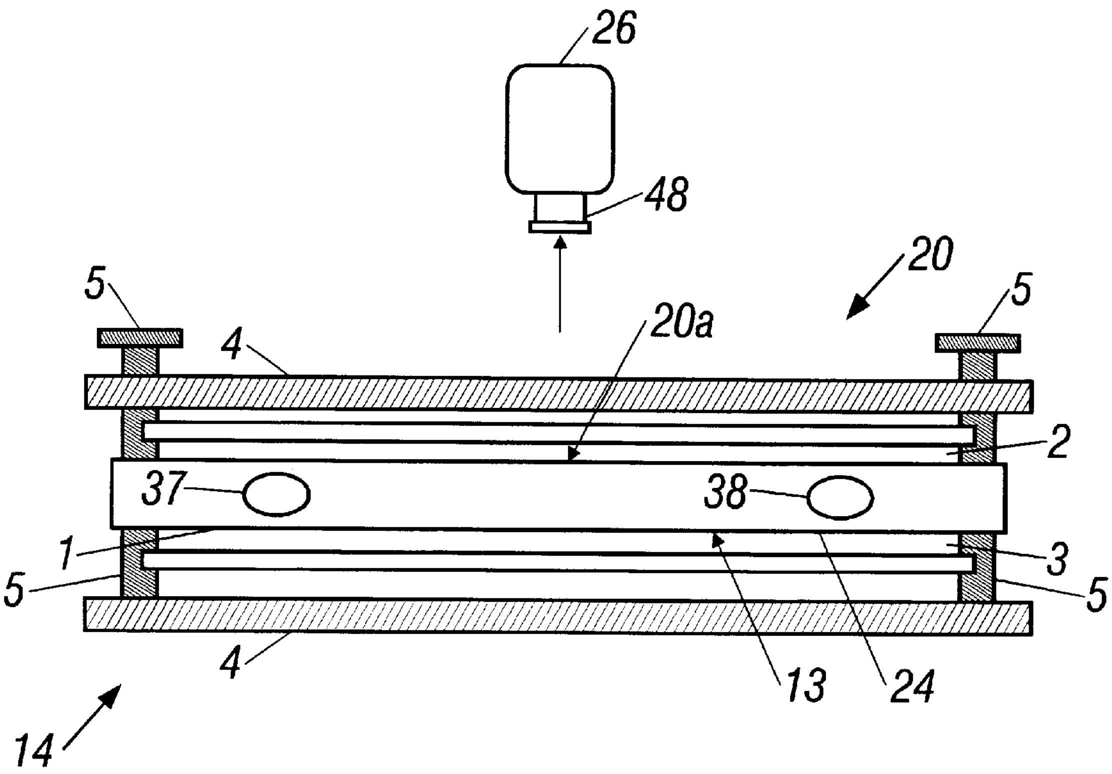
FIG. 3A is a representation of an apparatus from which water-borne microbes are imaged in accordance with an embodiment of the invention.

Referring to FIG. 3A, more detail is provided on the FOC 20. The FOC 20, from which images are taken, may be a modified fungal-growth chamber having, for example, a 2 mm thick spacer (e.g., silicon) or substantially transparent membrane 1 sandwiched between two glass microscope slides (2,3) forming the glass/spacer sandwich 14. The sandwich 14 may be held together with a stainless steel bracket 4 and attachment screws 5. A wall portion (surface 24) of the glass slide 3 is wetted by fluid 13. The microscope may be focused on surface 24 because it views through the glass slide 2 and because the spacer 14 has a slit or slot cut (not shown) all the way through it. With simple refocusing, the fluid 13-side of glass slide 2 would also be viewed. The cells in the fluid 13 flow over the glass slides 2 and 3 (surface 24). The interior dimensions of the chamber (i.e., the portion of chamber containing liquid) may be, for example, 30 mm by 5 mm by 2 mm. Liquid (e.g., fluid 13) may be routed by the pump 16 into the chamber through (FIG. 1) tube 37 (e.g., a 1/16" stainless steel tube) and out of the chamber through tube 38 (e.g., a 1/8" stainless steel tube). The influent 37 and effluent 38 tubes may be positioned such that a repeatable turbulent flow is achieved approximately in the center 20*a* of the FOC 20. (See FIGS. 1 and 3A). Adhesion may be measured with cells that attach near the center 20*a* of the chamber to surface 24 with the use of optical microscopy and image analysis.

Figure 4A:
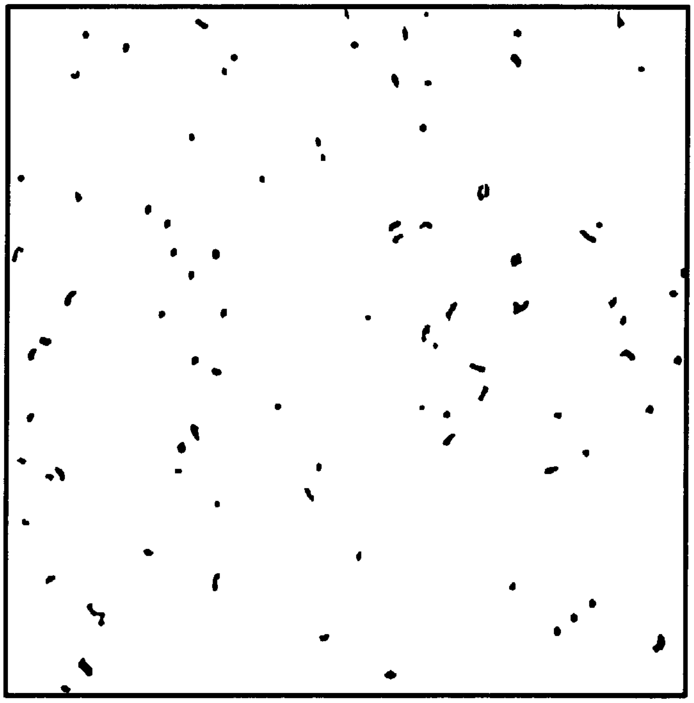
FIG. 4A is an image taken with a phase contrast microscope in accordance with an embodiment of the invention.
Figure 4B:
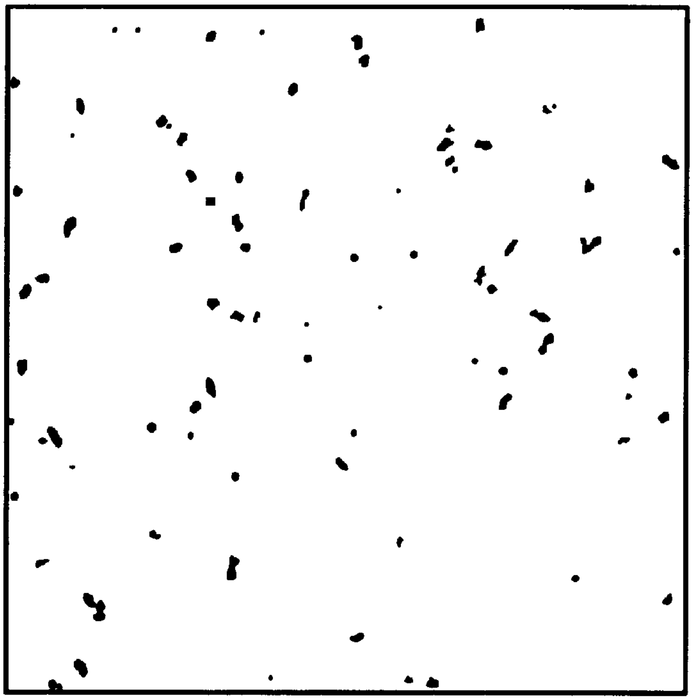
FIG. 4B is an image corresponding to the image of FIG. 3A which has been background subtracted by an image processor and binary converted by a frame grabber/processor in accordance with an embodiment of the invention.

The chamber may be mounted on the microscope 26 (e.g., on microscope stage 26*a*) for viewing. The microscope 26 and an objective 48 of the microscope 26 may be, for example, a Nikon Diaphot microscope available from Nikon Corporation (or equivalent) and a Plan 60/0.7 Ph3DL LWD 106/0-7-1.7 (or equivalent) objective, respectively. Images of sessile or planktonic particles from the FOC 20 which are collected with the video camera 27, under control of the camera controller 47, may be preprocessed for background subtraction and image enhancement in real-time using the image processor 30. The video camera 27 and the processor 30 may be, for example, a newvicon (or equivalent) video camera and an ARGUS 10 (or equivalent) image processor, respectively. Then, the frame grabber/processor 32, loaded with image analysis software may be used to grab (form binary representation of) two successive images (can be taken, for example, 1, 2, or 10 seconds apart) and store an average (in some alternative embodiments, instead of averaging, the images may be added) of these binary images in the storage device 35. Examples of an untouched image taken with a phase contrast microscope (which microscope 26 may be) and an image after operation of the ARGUS 10 image processor for background subtraction and binary conversion by a grabber/processor are shown in FIGS. 4A–B. The image analysis software is used for the final image analysis and is used to drive the image capture rate. The grabber/processor 32 and its image analysis software may be, for example, a Flashpoint Plus grabber card available from XpertMinds Corporation (or equivalent) and an Optimas image analysis system available from Optimas Corporation (or equivalent), respectively. The averaged image may be processed by thresholding the averaged image using the image analysis software and then using the software to count the thresholded objects to determine the number and total area of objects in the field of view (FOV) of the microscope 26. Using system 10 as described, it may be possible to provide quantitative information on the density and on the rate of increase (or decrease) of density of bacteria attached to solid surfaces (e.g., surface 24), or on planktonic bacteria in a potable-water-supply system.

System 10 implements a method of automated image analysis for continuous, real-time monitoring of attachment of microbes to (or detachment of microbes from) the surface 24 immersed in water containing microbes. Modifications of system 10 may also be used to investigate the effects of chemicals on these microbes. For example, system 10' (FIG. 5), which is a modification of system 10, may be used to assess the abilities of biocide chemicals to suppress biofilms in closed potable-water subsystems and may also be adaptable to similar investigations of biofilms in other water supplies.

Figure 5:
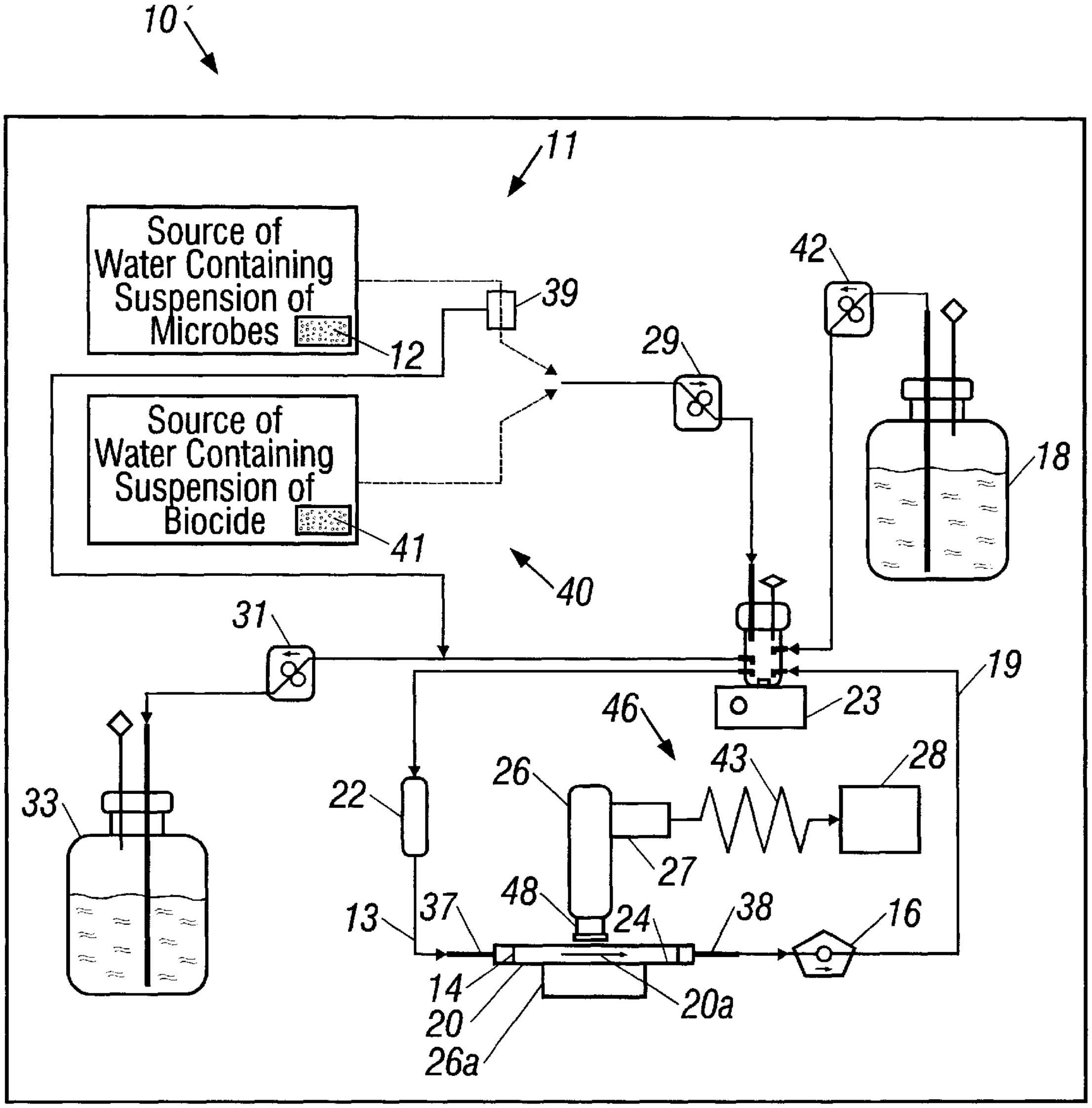
FIG. 5 is a representation of an apparatus for monitoring water-borne microbes that have attached themselves to a surface and for assessing the effects of a biocide on the microbes in accordance with an embodiment of the invention.
Figure 6A:
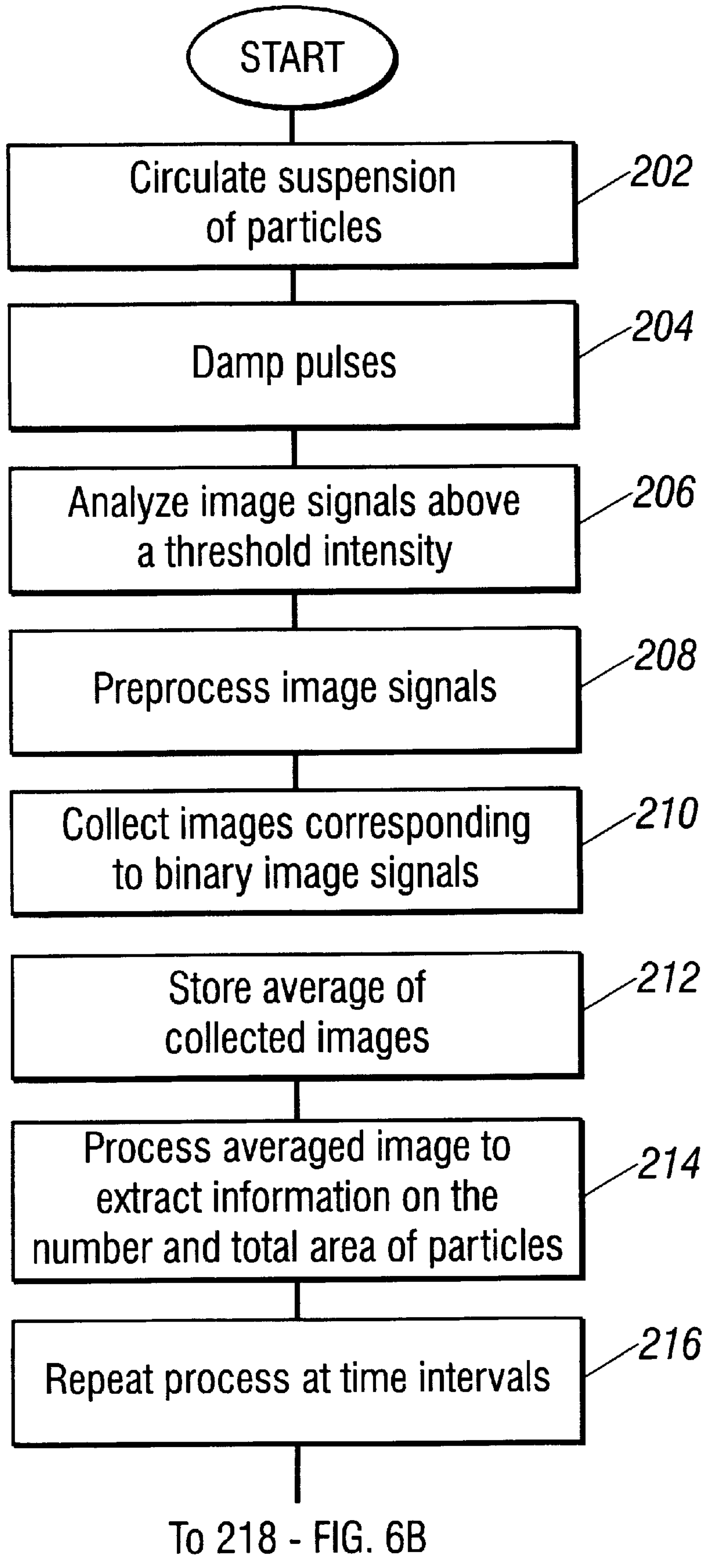
FIGS. 6A–C are a flowchart of a method of monitoring and treating particulate matter in accordance with an embodiment of the invention.
Figure 6B:
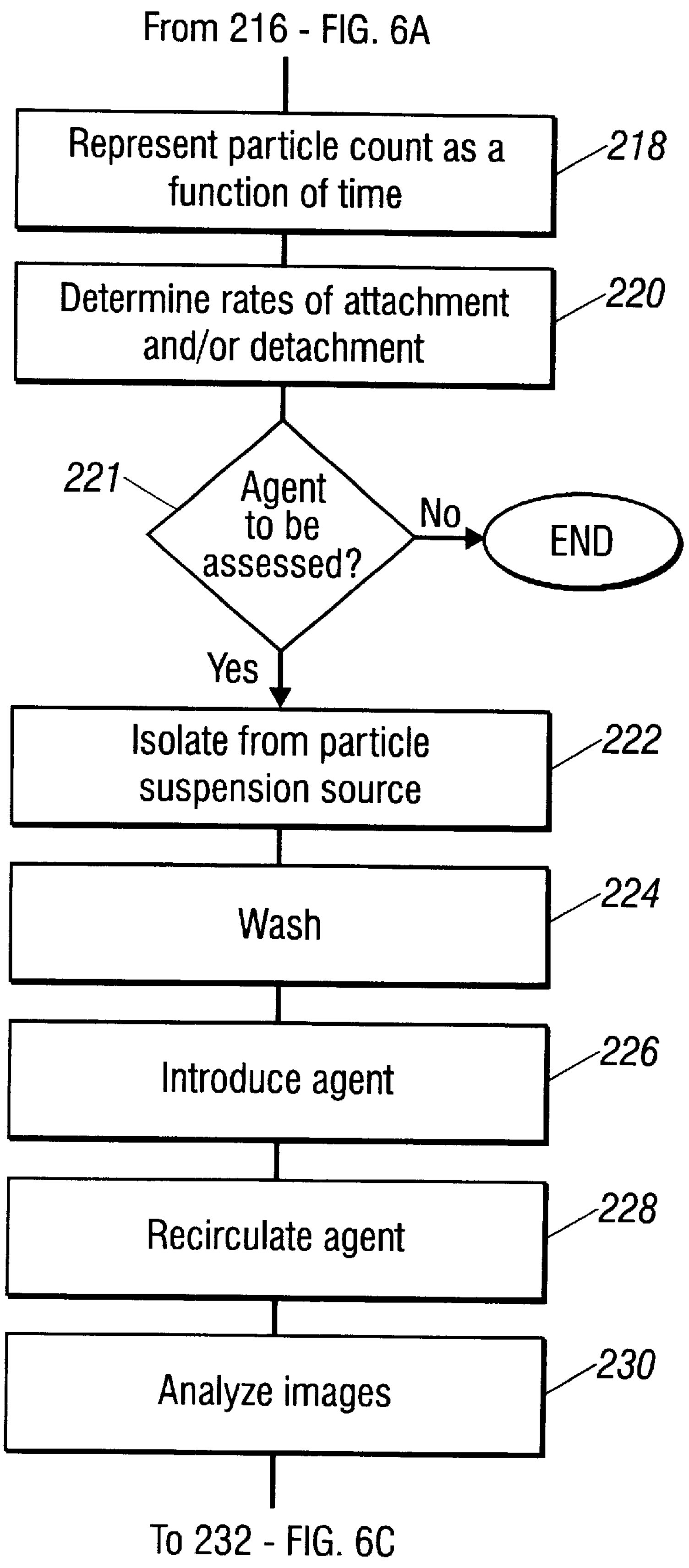
Figure 6C:
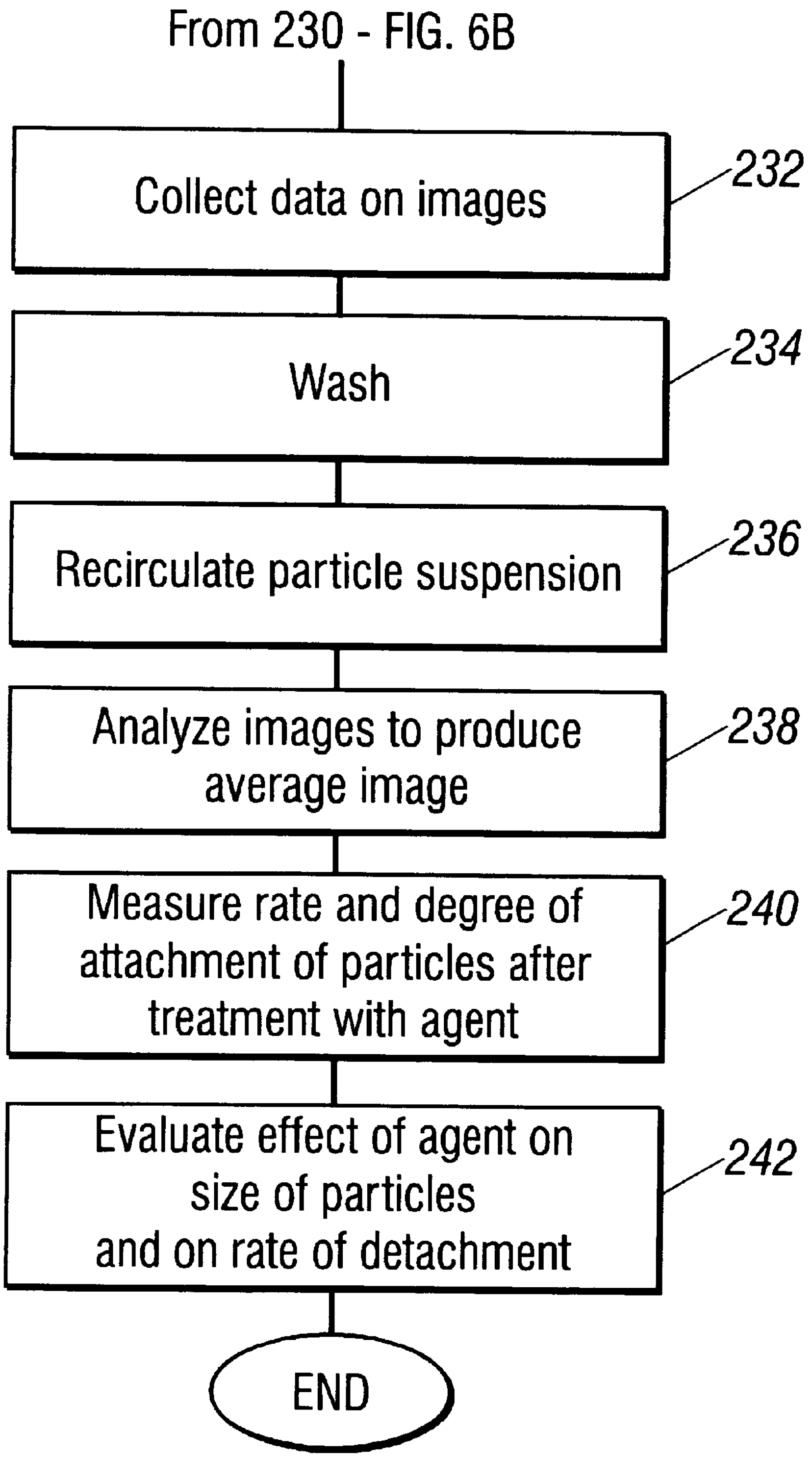
Figure 7A:
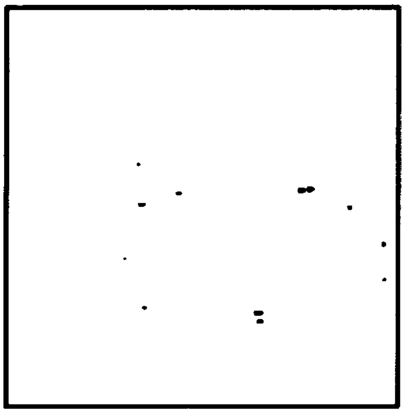
FIGS. 7A–F show a sequence of example sessile particle images which demonstrate the increased adhesion of microbes over time in accordance with an embodiment of the invention.
Figure 7B:
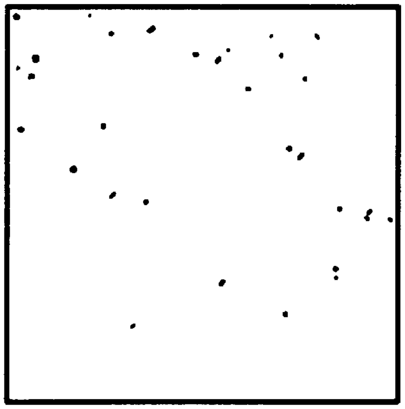
Figure 7C:
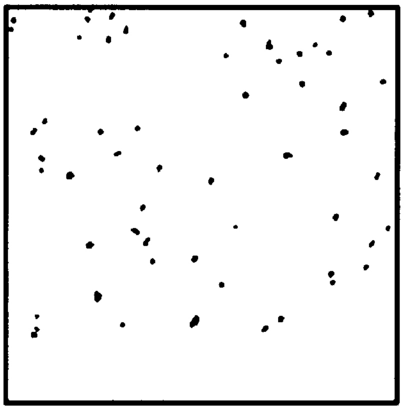
Figure 7D:
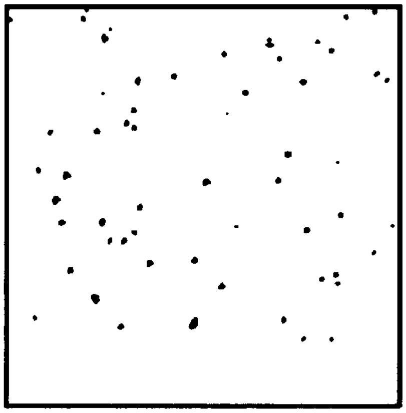
Figure 7E:
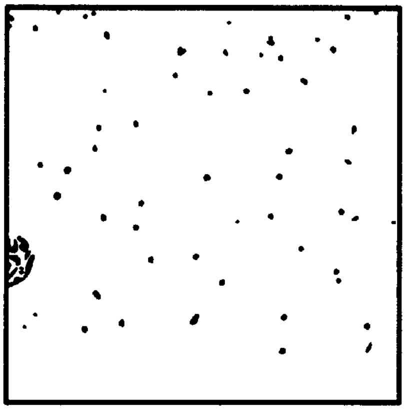
Figure 7F:
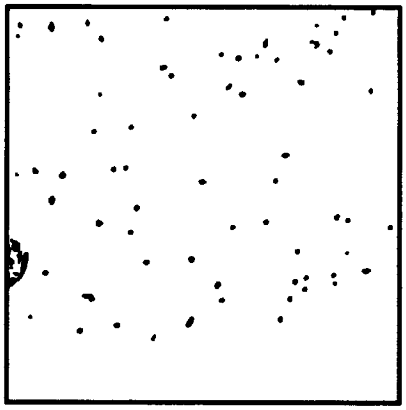

The analysis of biofilms and data gathering for the assessment of the effects of biocides on them is described in detail below with reference to system 10' of FIG. 5. For simplification of the drawings, FIG. 5 shows schematically the source of water 11 with only the suspension of microbes 12. Not all the elements of source 11 are shown. Although all elements of source 11 are not shown in FIG. 5, they are nevertheless meant to be included. FIG. 5 also shows schematically, for simplicity of the drawings, which includes system 10' a source 40 of water containing a suspension of biocide 41 coupled to the pump 29. Clearly, many ways could be used to introduce biocide 41 suspension to pump 29. It is to be understood that like elements shown in FIG. 5 of system 10' operate as described previously in reference to FIGS. 1 and 2 for system 10.

Referring to FIGS. 2, 5, and 6A–C with biocide not being introduced into the mixing vessel 23, water containing a suspension of microbes 13 from source 11 is circulated 202 through the FOC 20 (e.g., for 18 to 24 hours), during which time some microbes attach themselves to the surface 24. Examples which demonstrate the increased adhesion of microbes over time in images is shown in the sequence of FIGS. 7A–F for *Burkholderia cepacia* (*B. cepacia*). Water is recirculated through the recirculation loop 19 and the FOC 20 at a rate of, for example, 9.8 mL/min by the high-speed micropump 16. The pump 16 produces a pulsating flow, the pulses being damped 204 by the damping device 22 which may be positioned upstream of the FOC 20, as discussed previously. The influent 37 and effluent 38 tubes may be positioned to achieve turbulent flow approximately in the middle 20*a* of the FOC 20 where the monitored surface 24 is located. Turbulent flow may offer the advantage of randomizing the flow of microbes 12 (or biocide 41) in the FOC 20 which prevents flow-dependent microbe 12 (or biocide 41) buildup/removal (attachment/detachment) nonuniformities in monitoring adhesion and/or detachment of microbes 12, or in assessing the effects of the biocide 41.

Figure 8A:
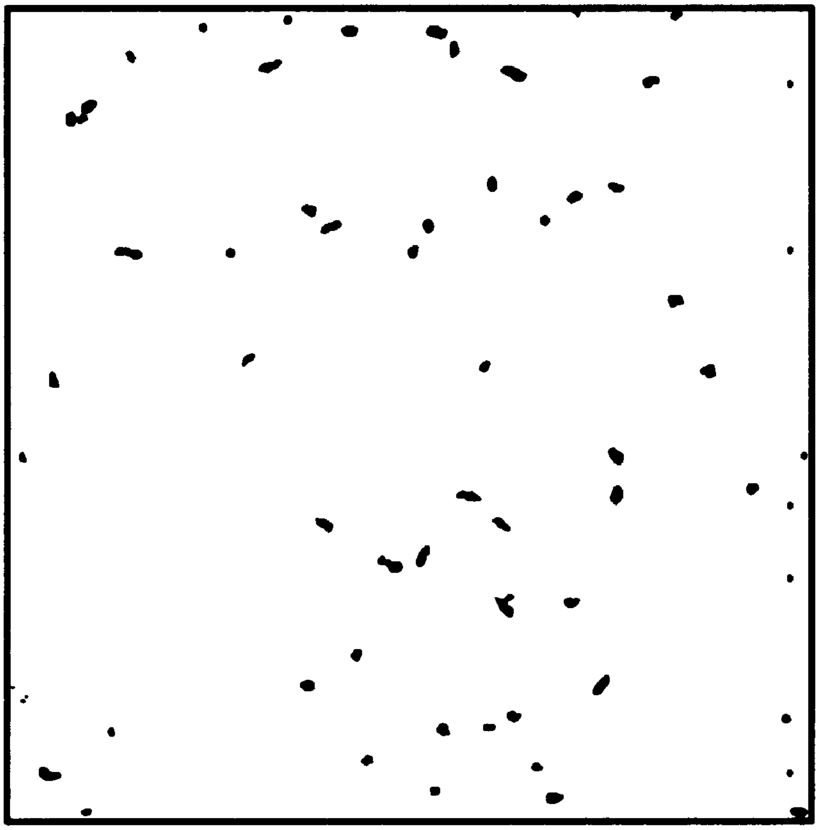
FIGS. 8A–B show first and second images of sessile particles and planktonic particles taken at two different times in accordance with an embodiment of the invention.
Figure 8B:
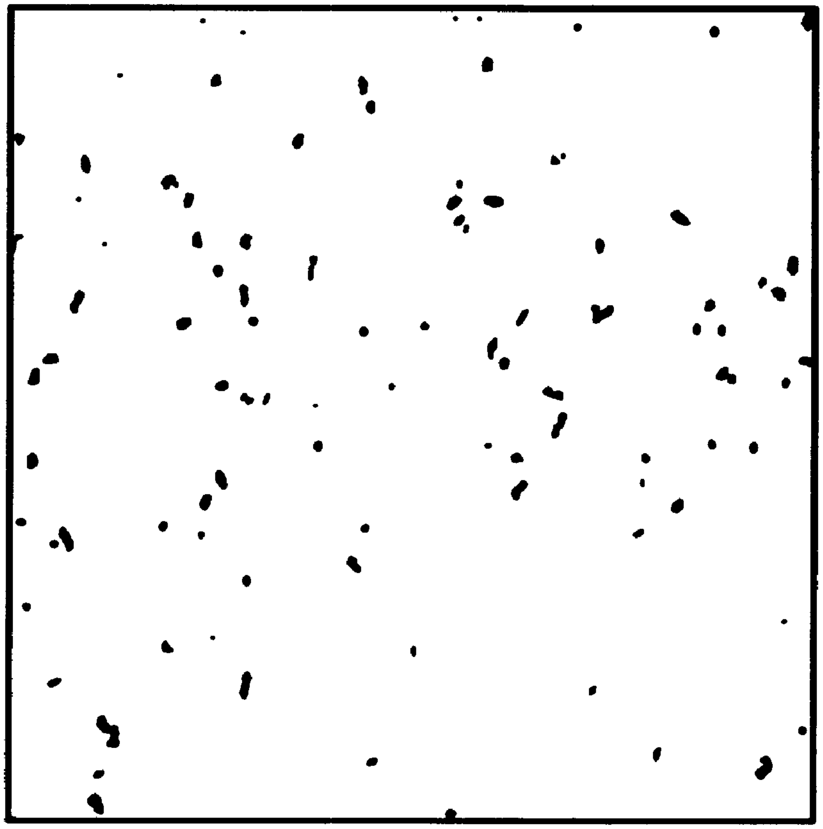
Figure 8C:
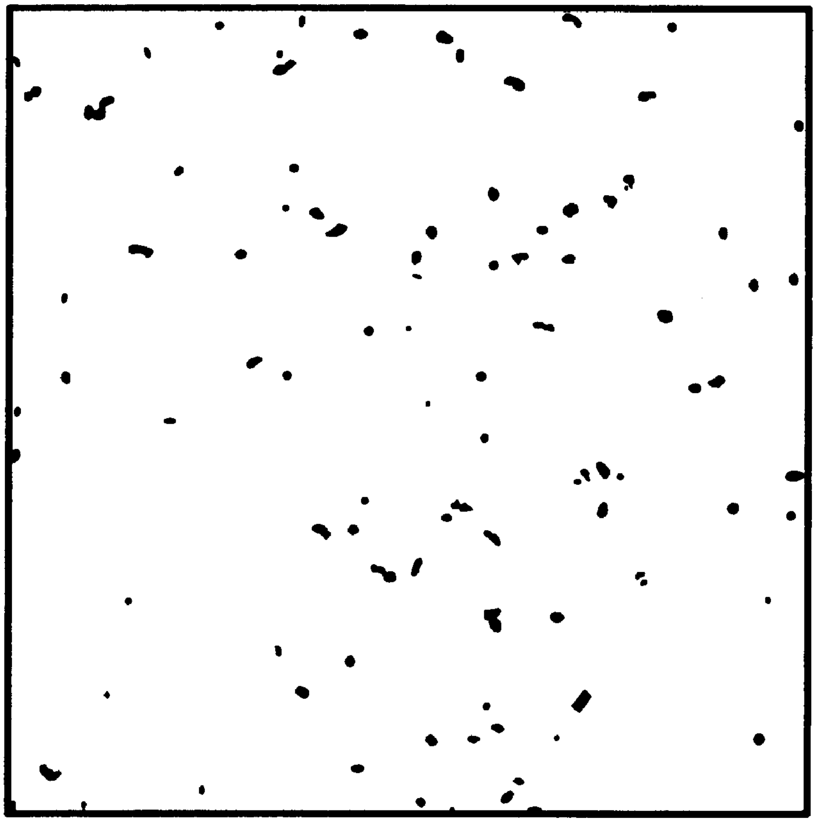
FIG. 8C shows an averaged image of the first and second images of FIGS. 8A–B in accordance with an embodiment of the invention.

Referring again to FIGS. 2, and 6A–C, image signals 43 from the video camera 27 above a threshold intensity are analyzed 206 during this time to acquire data on the rate and density of attachment of microbes 12. The video image signals 43 of the monitored surface 24 are preprocessed 208 into binary image signals 44. Then, the frame grabber 30 grabs 210 two successive images (first and second images or image sets taken at different times) corresponding to image signals 44 and stores 212 an average 45 of them in the storage device 35. Examples of the first, second and averaged images are shown in FIGS. 8A, 8B, and 8C, respectively. The averaged image 45 is processed 214 to extract information on the number and total area of objects (i.e., of attached microbes 12 (e.g., bacteria)) in the field of view of the microscope 26. This is done, as discussed previously, by setting a threshold intensity value for gray scale with, for example, the Optimas software in the grabber/processor 32 image. The objects (cells) having an image intensity above the threshold value are counted and sized. This information may be transferred to a spread sheet program and the pixel data may be converted to surface area and counts for each image.

The threshold intensity for analysis is selected to correspond with the intensity of data segments corresponding to only sessile particles captured in both the first and second images. In the averaged image (e.g., FIG. 8C), the intensity levels recorded in data segments corresponding to suspended (planktonic or moving) particles, captured in either of the first and second images (they appear white as do sessile particles in FIGS. 8A–B) are of lower levels than the intensity levels recorded for only sessile particles. This is because the first and second images by themselves are instantaneous (frozen) images which cannot distinguish between planktonic or sessile particles. If the same planktonic particle appears in both the first and second images, it will appear in different places. However, in the averaged image, since the planktonic particles are moving, they will appear gray in an average unlike the sessile particles which will appear white (see FIG. 8C). Therefore, proper threshold adjustment for analysis of the average image will allow the sessile particles to be counted while the planktonic particles may be discarded.

If, however, it is desired to study planktonic particles, another adjustment may be made in the threshold intensity for analysis of the averaged image that eliminates white sessile particles and counts gray planktonic particles. This process may be repeated 216 at time intervals, yielding cell counts that may be represented (e.g., plotted 218 on the display device 36) as a function of time, to determine 220 rates of attachment to and/or detachment from surface 24 (see FIGS. 2 and 9 which will be discussed below).

Referring again to FIGS. 2, 5, and 6A–C, if biocide 41 is to be assessed 221, the FOC 20 and its recirculation loop 19 with the high-speed micropump 16 are isolated 222 from the source of the cell suspension 11 by closing the adaptor valve 39 and washed 224 with deionized water (e.g., with 300 mL) from source 18. With valve 39 closed, excess microbes may be discarded to the waste tank 33 through pump 31. Next, water containing the biocide 41 to be tested from the source 40 is pumped 226 into the FOC 20 and recirculated 228 through the recirculation loop 19 and the FOC 20 for a period of time, for example, for 5 to 6 hours. The water from source 18 may be used to adjust biocide concentration in mixing vessel 23 when assessment of a biocide 41 is to be performed.

While the water containing biocide 41 is recirculated, more images (e.g., two successive images) corresponding to image signals 49 (similar to image signals 44) are analyzed 230 and data collected 232 as described below. This is followed by another wash cycle 234 from source 18, which is followed by another cycle of recirculation 236 of the cell suspension and analysis 238 of the images corresponding to image signals 49. The analysis produces an average image (may appear similar to FIG. 8A which may be stored) (similar to image 45) which is used (similarly to what was described previously) to measure the rate and degree of attachment on the surface 24 after the treatment 240 with the biocide 41. Although more than two images (or images sets) may be used, only two may be needed to define the moving (planktonic) verses nonmoving (sessile) cells.

Video image signals 43 may be acquired at a frequency of, for example, once an hour (or more often) to measure the rate of attachment, and the images corresponding to image signals 49 are acquired, for example, every 20 minutes (or more often) to evaluate 242 the effect of the biocide 41 on the size of the microbe 12 biofilm and on the rate of microbe 12 detachment.

A system similar to the continuous optical biofilm measurement system 10' was used to observe the attachment and removal of microbes from surfaces (similar to surface 24). The system was also used to determine the efficacy of oxidizing biocides on the removal of microbes, for example, *B. cepacia* from the surfaces similar to surface 24. Microbes were isolated in a water processing system and the isolate was identified as *B. cepacia* by a commercial automated identification system (available from Vitek Corporation) with identification confirmed by another identification system (available from Biolog Corporation). The culture was maintained on agar, and inoculation cultures were grown in a modified DworkinFoster medium (DFM) (similar to medium 15) consisting of: 4.0 g potassium phosphate monobasic; 6.0 g sodium phosphate dibasic; 0.2 g magnesium sulfate pentahydrate; 0.4 g ammonium chloride; 20 g fructose; 1.0 mg ferrous sulfate; 0.01 mg boric acid; 0.01 mg manganous sulfate; 0.07 mg zinc sulfate; 0.05 mg copper sulfate; and 0.01 mg molybdic acid, per liter, at approximately pH 6.75. The fermentation system (similar to fermentor 17) was a Bioflow III fermentor available from New Brunswick (or equivalent) could have been used. The fermentor attached to a series of mixing chambers (similar to mixing vessels 21 and 23) that allowed dilution of the culture and control of the cell concentration in the attachment cell/optical chamber (similar to FOC 20). All chemicals were reagent grade and the media filter sterilized and made with Milli-Q (available from Millipore Corporation) water (or equivalent). The *B. cepacia* was maintained on DFM at a dilution rate of approximately 0.0195/hr. The dilution rate of one (the first) of the mixing vessels (similar to mixing vessel 21) was approximately 0.276/hr and approximately 2.129/hr for the other (the second) mixing vessel (similar to mixing vessel 23). The bacterial concentration for the fermentor and the first mixing vessel was approximately $1.8\times10^9$ CFU/mL while it was approximately $2.34\times10^7$ CFU/mL for the second mixing vessel. The *B. cepacia* continuous culture was allowed to attain steady state. After steady state was reached, the adhesion experiments progressed.

The biocides (similar to biocides 41) were prepared as follows. Ozone was made continuously with a Fisher Ozon generator 500M available from Fisher (or equivalent) attached to a 1.5-L Teflon™ (or equivalent) bottle, and ozone concentration was measured spectrophotometrically. Chlorine was made by dilution of commercially obtained bleach. Free chlorine was determined using the well known N,N-diethyl-p-phenylenediamine (DPD) method. Iodine was made as a stock solution of KI and I, and the concentration determined by the DPD method.

For all these adhesion and biofilm treatment trials (experiments), the flow rate of the cell suspension and biocide treatment stream through the FOC was 9.8 mL/min. First, cells were allowed to attach to the FOC surface (similar to surface 24) for approximately 18–24 hr, during which time video image signals (similar to video image signals 43) were acquired. Then the FOC and high-speed micropump (similar to pump 16) were isolated from the main fermentation system (similar to fermentor 17) using an adapter or flow around valve (similar to valve 39) as discussed, and washed with approximately 300 mL of deionized water from a source (similar to source 18). The valve 39 was then closed and the FOC was attached to a source of biocide treatment solution (similar to source 40 of biocide 41) containing 1 L of the biocide solution. The fluid from the biocide source was then recirculated through the FOC at approximately 9.8 mL/min for approximately 5–6 hr. during which time images corresponding to image signals (similar to image signals 49) were acquired. The FOC and high speed pump were then washed with another approximately 300 mL of deionized water, and the FOC was reattached to the main fermentation system. Cells were allowed to attach to surfaces previously treated with biocide for approximately 18–24 hours and then the biocide treatment was repeated. Video image signals (similar to video image signals 43) were acquired at least every hour to measure attachment rate. Images corresponding to image signals (similar to image signals 49) were acquired at least every 20 minutes to evaluate the effect of the different biocides on cell size and detachment.

The results of these trials are shown in FIGS. 6–9. For the results in FIGS. 9–12, the total microscope (e.g., similar to microscope 26) FOV area analyzed for all trials was 3,000 $\mu m^2$. At least three trials were completed and the results averaged for each adhesion profile (see FIGS. 10–12). Adhesion rates (FIG. 9) were determined using a regression plot of the data from the three trials, each using averaged images.

Figure 9:
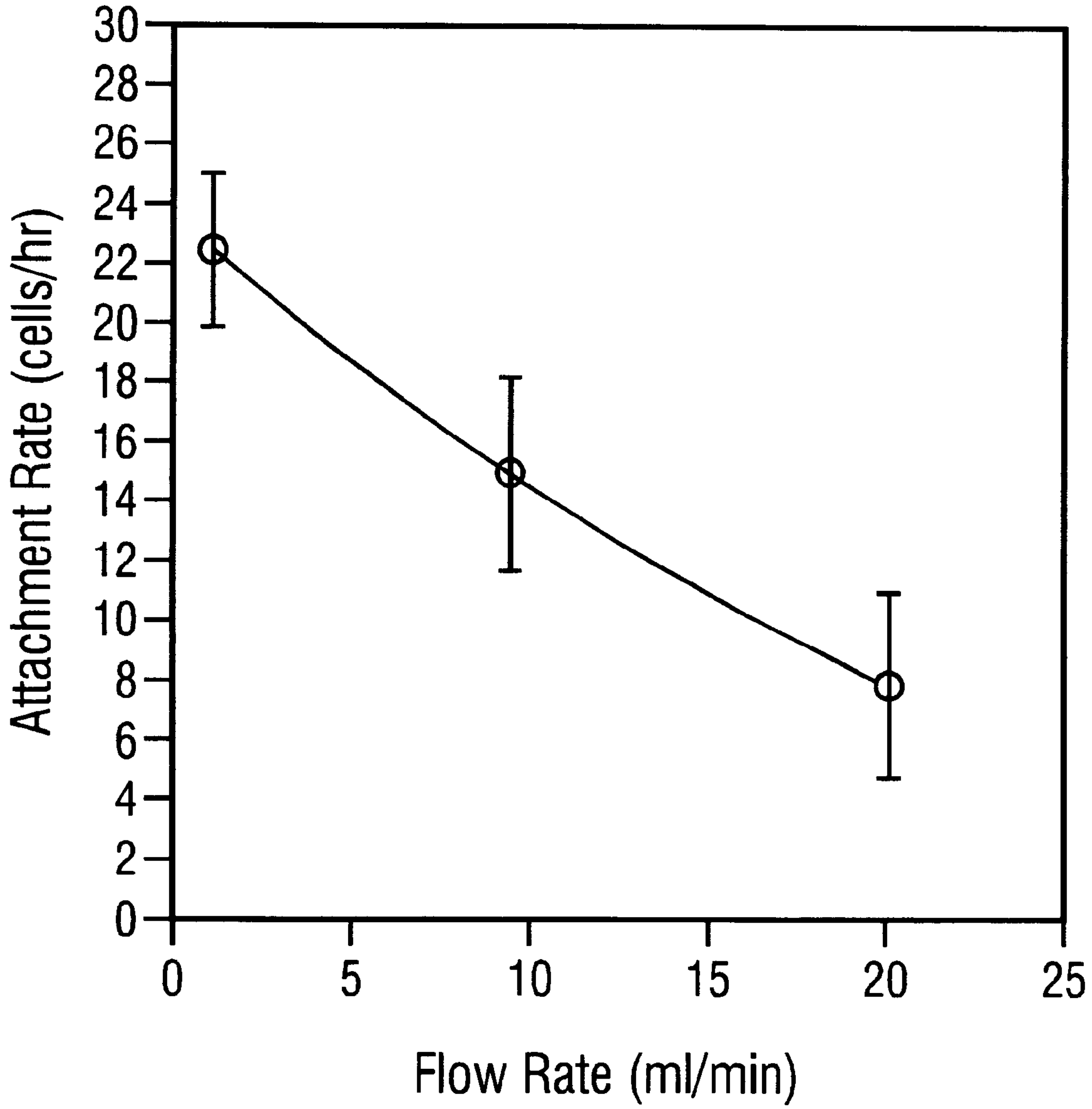
FIG. 9 is a plot of attachment rate versus flow rate for data collected from a system in accordance with an embodiment of the invention.

Referring to FIG. 9, the effect of flow rate on the attachment rate of *B. cepacia* is illustrated. It is observed that the cell attachment rate decreases on the surface in the FOC as the flow rate increases, as would be expected. The data are means ± the standard deviation (SD) of three trials.

Figure 10:
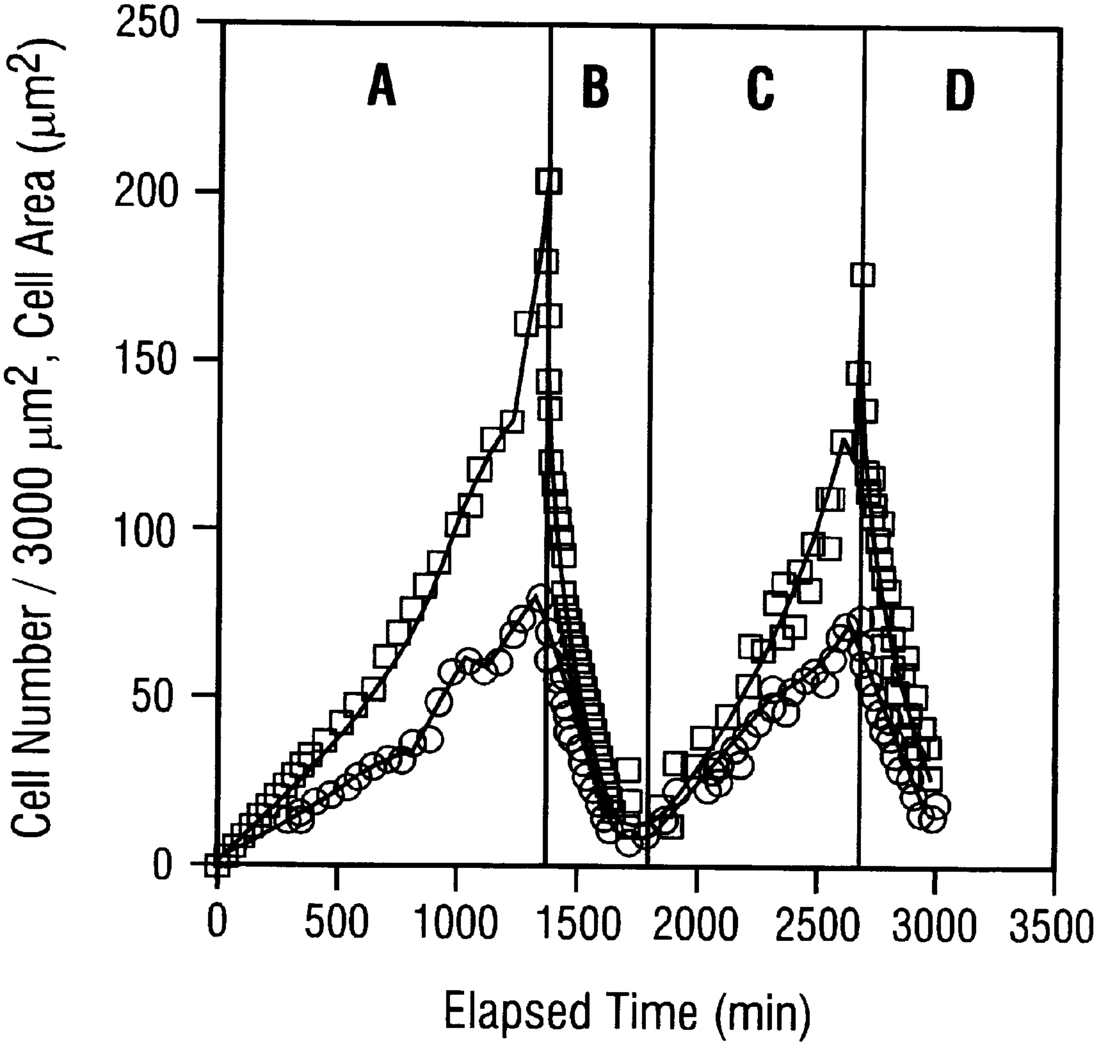
FIGS. 10–12 are plots of data collected from a system in accordance with an embodiment of the invention used to assess the effects of different biocides on cell number/cell area versus time.
Figure 11:
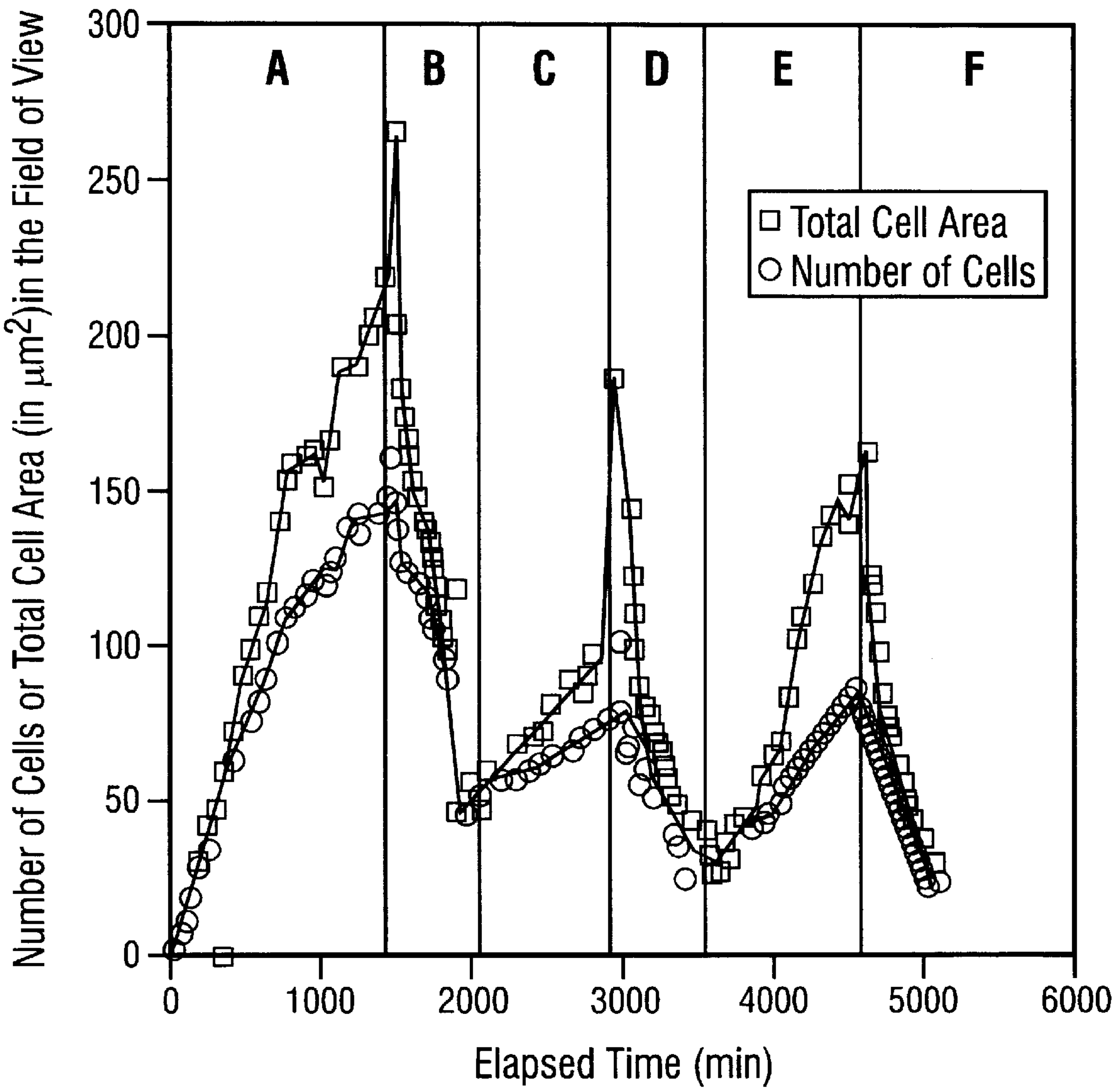
Figure 12:
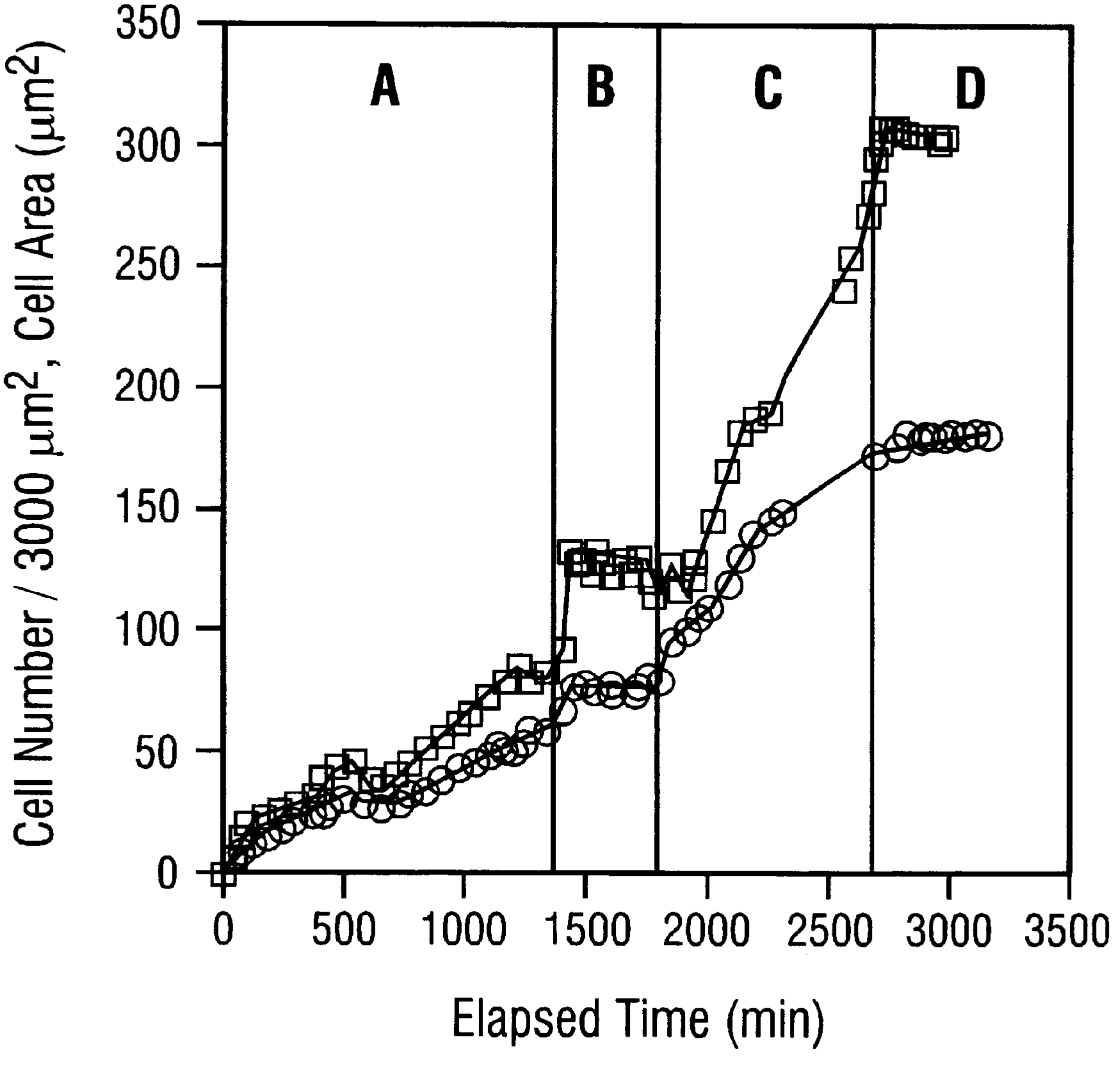

FIG. 10 shows both cell density (cell number/3000 $\mu m^2$) and cell area (in $\mu m^2$) as a function of elapsed time for the treatment of a *B. cepacia* biofilm with ozone. In FIG. 7, different regions or phases may be identified. For example, regions A=adhesion, B=treatment with 2 ppm ozone, C=adhesion, and D=treatment with 2 ppm ozone. The squares in FIG. 7 are for total cell area and the circles are for cell number, and the data are means of three trials. FIGS. 11 and 12 similarly show means of three trials each for the effects of treatment of *B. cepacia* biofilms with chlorine and iodine, respectively. In FIG. 11, the legend explains the regions. In FIG. 12, regions A=adhesion, B=treatment with 24 ppm iodine, C=adhesion, and D=treatment with 48 ppm iodine. It appears from these data that biocide efficacy was greatest for ozone, followed by chlorine, and then iodine.

One aspect of the implementations described above is that they may contain all the fluids in a closed system, and thus may allow for processing of a sample without leakage of the fluid out of the apparatus. The three-way adapter valve 39 allows for the closed system operation of this hardware.

The system 10' (and 10) may distinguish between planktonic and sessile cells through the use of the processor 32 for enhanced image processing. The system 10' (and 10) may directly measure a single cell attached to the surface 24. The system 10' (and 10) not only samples biofilm, but also directly measures and quantitates the biofilm microbes. Implementations of the invention may look at single cells as well as colonies, can be used with a variety of substrates (surfaces 24), as discussed previously, and may also be used as a tool for monitoring sessile bacteria in flowing streams. In implementations of the invention, at least one subsequent image (or image set), for example, but not limited to, a second or later image, may be processed along with the first image (or image set) to provide an indication of any changes in the accumulation of sessile particles during a selected time period (e.g., an hour or a day).

Figure 13:
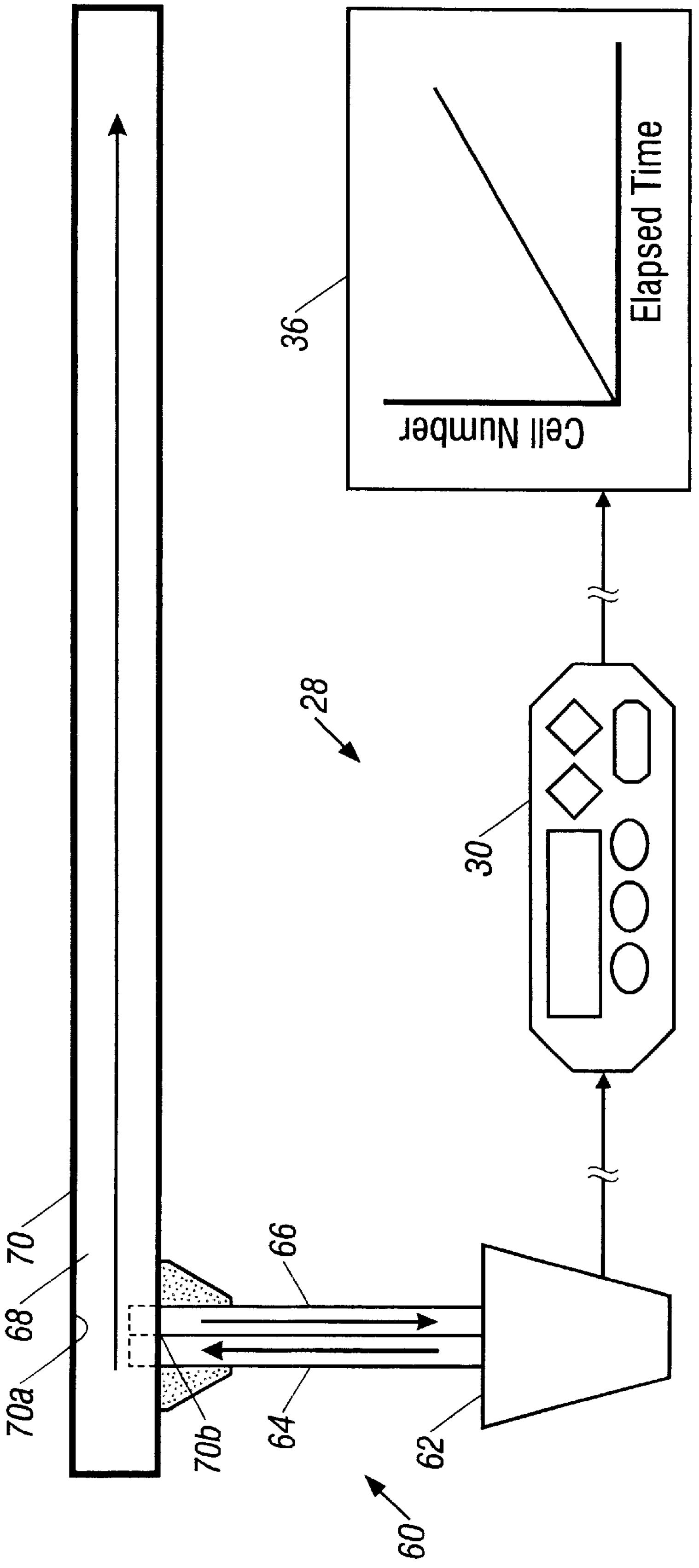
FIG. 13 is a representation of an apparatus for an optical and image processing system in accordance with another embodiment of the invention.

In implementations of the invention, determination of microbial loads may be made in water samples processed in various environments. In other implementations of the invention, it may be possible to monitor any water source for microbial load that can be cultured. An exemplary system 60 for in-line monitoring of microbial biofilm load is shown in FIG. 13. System 60 includes a reflective microscope with low light camera 62 (functions similarly to microscope 26 with camera 27), and a pair of fiber optic bundles or cables 64 and 66. Fiber optic bundles 64 and 66 are inserted into a fluid 68 within a fluid line/water tank 70 and properly sealed to prevent leakage. Fluid line/water tank 70 may be similar to line 19 (or FOC 20) and fluid 68 may be similar to fluid 13. Fiber optic bundle 64 carries light from a light source (not shown) associated with reflective microscope with low light camera 62 to impinge on the fluid 68 to illuminate microbial biofilm (or planktonic particles) for assessment of biofilm (microbe) growth and/or biocide efficacy. Light from the light source is reflected from biofilm (e.g., off a surface 70*a* of line/tank 70) or planktonic particles (in fluid 68) and images of them are collected by fiber optic bundle 66 which pass to the image processor 30 for data presentation on device 36 as shown in FIG. 13. For simplicity of the drawings, not all elements of image processing system 28 are shown in FIG. 13, but it is to be understood that they are meant to be included. In alternative embodiments, instead of fiber optic bundles 64 and 66 being inserted in the fluid line/water tank 70, they may abut the outer surface 70*b* of fluid line/water tank 70 to view the fluid 68 if the outer surface is light transparent.

Although specific embodiments have been disclosed, other embodiments and implementations of the invention are contemplated within the scope of the following claims.

What is claimed is:

1. An apparatus for monitoring particulate matter in a fluid container or conduit, comprising:

- a wall portion that supports sessile particles derived from the fluid;
- means for forming images of the sessile particles and particles suspended in the fluid adjacent the wall portion;
- means for producing data corresponding with the images of the sessile particles and suspended particles;
- means for processing data corresponding to the images of the sessile particles and the suspended particles, and for removing data corresponding to the suspended particles, and for producing an output data segment corresponding substantially exclusively to the sessile particles present in the images; and
- means for processing the output data segment and deriving an output signal representative of the accumulation of sessile particles on the wall portion, wherein the means for processing the output data segment comprises image analysis means for quantifying data segments corresponding to sessile particles on the wall portion.

2. The apparatus of claim 1, wherein the means for processing the output data segment comprises means for filtering and removing data segments corresponding with intensity levels below the threshold level.

3. The apparatus of claim 1, wherein the means for forming images comprises means for forming a first image and a second image at a time subsequent to the formation of the first image, and wherein the means for processing the output data segment comprises image analysis means for quantifying data segments corresponding to sessile particles that have an intensity falling above a threshold intensity level.

4. The apparatus of claim 3, wherein the threshold intensity level is selected to correspond with the intensity of data segments corresponding to sessile particles captured in both the first and second images, and wherein the intensity levels recorded in data segments corresponding to suspended particles, captured at respective locations in only one of the first and second images, are of lower levels than the intensity levels corresponding to sessile particles captured at the same location in both images.

5. The apparatus of claim 1, further comprising means for assessing the effect of an agent on the sessile particles.

6. The apparatus of claim 1, wherein the means for forming images comprises means for forming a first image and a second image at a time subsequent to the formation of the first image.

7. The apparatus of claim 6, wherein the first and second images comprise a first image set, further comprising means for deriving at least one subsequent image set and for processing data derived from the first and at least one subsequent image set to provide an indication of any changes in the accumulation of sessile particles during a selected time period.

8. The apparatus of claim 6, wherein the means for processing data comprises means for processing data corresponding to the first and second images, the output data segment corresponding to the sessile particles present in both the first and second images.

9. An apparatus for monitoring microbial matter within a fluid container, comprising:

- a wall portion that supports sessile organisms derived from organisms present in the fluid;
- means for forming images of sessile organisms adhered to the wall portion and planktonic organisms in the fluid adjacent the wall portion;
- means for digitizing and processing data corresponding to the images of sessile and planktonic organisms and for producing output data segments corresponding to the sessile organisms present in the images; and
- means for processing the output data segments and deriving an output signal corresponding substantially exclusively to the accumulation of sessile organisms on the wall portion.

10. The apparatus of claim 9, wherein the means for forming comprises means for forming a first image and for forming a subsequent second image of the sessile organisms and planktonic organisms in the fluid adjacent the wall portion.

11. The apparatus of claim 9, further comprising means for assessing the effects of biocide on the sessile organisms.

12. The apparatus of claim 11, wherein the means for assessing the effects of biocides on sessile organisms comprises a second container having a biocide suspension, and valving means, associated with the first and second containers and with the wall portion, for providing fluid communication between the wall portion and a selected one of the first and second containers.

13. A method of monitoring particulate matter, comprising:

- supporting sessile particles derived from a fluid;
- forming images of the sessile particles and of particles suspended in the fluid; and processing data corresponding to the images of sessile particles and suspended particles to produce an output data segment corresponding substantially exclusively to the sessile particles present in the images and to derive an output signal corresponding to the accumulation of sessile particles.

14. The method of claim 13, further comprising assessing the effect of an agent on the sessile particles.

15. A method of monitoring microbial matter within a fluid container, comprising:

supporting sessile organisms, derived from organisms present in the fluid, on a surface of the container;

forming images of the sessile organisms adhered to the surface and of planktonic organisms in the fluid adjacent the surface; and processing data corresponding to the images to produce an output data segment corresponding substantially exclusively to the sessile organisms present in the images and to derive an output signal corresponding to the accumulation of sessile organisms on the surface of the container.

16. The method of claim 15, further comprising assessing the effect of biocide on the sessile organisms.

17. An apparatus for monitoring particulate matter in a fluid container or conduit, comprising:

a wall portion that supports sessile particles derived from the fluid; and an optical and image processing system connected to:

form images of the sessile particles and of particles suspended in the fluid adjacent the wall portion, digitize and process data representative of the images of sessile particles and suspended particles, and filter the data to remove data corresponding to images of suspended particles, and to produce output data segments representative only of the sessile particles present in the images, and process the output data segments and derive an output signal representative of the accumulation of sessile particles on the wall portion.

18. The apparatus of claim 17, wherein the optical and image processing system comprises a microscope.

19. The apparatus of claim 17, wherein the optical and image processing system comprises an image processor.

20. The apparatus of claim 17, wherein the optical and image processing system comprises a frame grabber.

21. The apparatus of claim 17, wherein the optical and image processing system comprises a storage device which stores the images.

22. The apparatus of claim 17, wherein the optical and image processing system comprises a display device.

23. The apparatus of claim 17, wherein the optical and image processing system comprises a video monitor.

24. The apparatus of claim 17, wherein the wall portion forms a portion of a flow chamber and an optical cell.

25. An apparatus for monitoring microbial matter within a fluid container, comprising:

a wall portion that supports sessile organisms derived from organisms present in the fluid;

a microscope which forms images of sessile organisms adhered to the wall portion and planktonic organisms in the fluid adjacent the wall portion;

a camera coupled to the microscope which forms video signals representative of the images;

a first processor coupled to the camera which processes data representative of the images of sessile organisms and planktonic organisms and produces an output data segment representative of the sessile organisms present in the images; and a second processor coupled to the first processor which processes the output data segment and derives an output signal representative of the accumulation only of sessile organisms on the wall portion.

26. The apparatus of claim 25, wherein the data segment is representative of sessile particles that have an intensity falling above a threshold intensity level.

27. The apparatus of claim 25, wherein the data segment is filtered to remove data representative of intensity levels below a threshold level.

28. The apparatus of claim 25, further comprising a source of biocide which introduces the biocide into the fluid to assess the effect of the biocide on the sessile particles.

29. The apparatus of claim 25, wherein the wall portion forms a portion of a flow chamber and an optical cell.

30. The apparatus of claim 29, further comprising valving means for selectively coupling the flow chamber to a selected one of the source of biocide and the fluid container.

31. The apparatus of claim 25, wherein the microscope forms a first image and a subsequent second image of the sessile organisms and planktonic organisms in the fluid adjacent the wall portion.

32. The apparatus of claim 25, wherein the second processor comprises image analysis code which enumerates the data segment representative of the sessile particles that have an intensity falling above a threshold intensity level.

33. The apparatus of claim 25, wherein the microscope forms a first image set and a subsequent image set, and wherein the second processor processes signals representative of the image sets to provide an indication of any changes in the accumulation of sessile particles during a selected time period.

34. The apparatus of claim 25, the wall portion disposed remotely from the microscope, the apparatus further comprising at least one optical cable having one end optically coupled with the microscope and another, distal end, and further comprising coupling means for optically connecting the distal end with the wall portion for transmitting images of sessile and suspended particles adjacent the wall portion to the microscope.

* * * * *